(12) United States Patent
Treskow et al.

(10) Patent No.: US 11,884,618 B2
(45) Date of Patent: *Jan. 30, 2024

(54) PREPARATION OF (METH)ACRYLIC ACID ESTERS

(71) Applicant: EVONIK OPERATIONS GMBH, Essen (DE)

(72) Inventors: Marcel Treskow, Darmstadt (DE); Silvia Beyer, Ober-Ramstadt (DE); Thorben Schütz, Alsbach-Hähnlein (DE); Steffen Krill, Mühltal (DE)

(73) Assignee: Evonik Operations GmbH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/750,273

(22) Filed: May 20, 2022

(65) Prior Publication Data

US 2022/0281798 A1 Sep. 8, 2022

Related U.S. Application Data

(63) Continuation of application No. 17/268,463, filed as application No. PCT/EP2019/070593 on Jul. 31, 2019.

(30) Foreign Application Priority Data

Aug. 16, 2018 (EP) .................... 18189276

(51) Int. Cl.
*C07C 67/08* (2006.01)
*B01J 27/138* (2006.01)
*B01J 31/02* (2006.01)
*C07C 69/54* (2006.01)

(52) U.S. Cl.
CPC ............ *C07C 67/08* (2013.01); *B01J 27/138* (2013.01); *B01J 31/0232* (2013.01); *C07C 69/54* (2013.01); *B01J 2231/324* (2013.01); *B01J 2531/002* (2013.01)

(58) Field of Classification Search
CPC ............ B01J 2231/324; B01J 2531/002; B01J 27/138; B01J 31/0232; B01J 21/10; C07C 67/08; C07C 69/54; C07C 2521/10
See application file for complete search history.

(56) References Cited

U.S. PATENT DOCUMENTS

| | | | |
|---|---|---|---|
| 4,458,007 A | 7/1984 | Geissler et al. | |
| 4,540,743 A | 9/1985 | Schulz et al. | |
| 5,080,998 A | 1/1992 | Irving | |
| 6,281,271 B1 | 8/2001 | Rumphorst et al. | |
| 6,384,238 B1 | 5/2002 | Zicar | |
| 7,659,425 B2 | 2/2010 | Weikard et al. | |
| 11,319,276 B2 | 5/2022 | Treskow et al. | |
| 11,414,373 B2 | 8/2022 | Hartmann et al. | |
| 2005/0250923 A1 | 11/2005 | Palmese et al. | |
| 2006/0173213 A1 | 8/2006 | Chen | |
| 2009/0001322 A1 | 1/2009 | Wiesler et al. | |
| 2012/0219885 A1 | 8/2012 | Fäcke et al. | |
| 2013/0022914 A1 | 1/2013 | Tanaka et al. | |
| 2015/0232409 A1 | 8/2015 | Misske et al. | |
| 2016/0229863 A1 | 8/2016 | Hillmyer et al. | |
| 2016/0289160 A1 | 10/2016 | Oba et al. | |
| 2017/0022142 A1 | 1/2017 | Knebel et al. | |
| 2017/0088502 A1 | 3/2017 | Goto et al. | |
| 2019/0352251 A1 | 11/2019 | Hartmann et al. | |
| 2020/0331845 A1 | 10/2020 | Treskow et al. | |
| 2021/0163439 A1 | 6/2021 | Treskow et al. | |
| 2021/0179531 A1 | 6/2021 | Treskow et al. | |

(Continued)

FOREIGN PATENT DOCUMENTS

CS 200 395 9/1980
EP 2 899 214 7/2015

(Continued)

OTHER PUBLICATIONS

Clark et al. (A One-Step Procedure for the Monoacylation of Symmetrical 1,2-Diols, J. Org. Chem., 67, pp. 5226-5231, Published Jun. 2002) (Year: 2002).*
FR2739850 translated (Year: 1997).*
JP 1995 07 017940 translated (Year: 1995).*
Notice of Allowance for copending U.S. Appl. No. 17/268,463, dated Nov. 9, 2022.

(Continued)

*Primary Examiner* — Yevgeny Valenrod
*Assistant Examiner* — Blaine G Doletski
(74) *Attorney, Agent, or Firm* — Law Office of Michael A. Sanzo, LLC

(57) ABSTRACT

The invention relates to a method for preparation of (meth)acrylic acid esters from (meth)acrylic acid anhydrides. The method involves: reacting a (meth)acrylic acid anhydride of Formula (I):

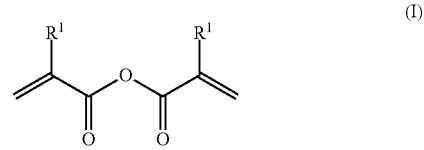

wherein $R^1$ is a hydrogen atom or a methyl group;
with a substrate in the presence of a first catalyst to form a product mixture comprising the (meth)acrylic acid ester; and wherein:
the substrate is selected from the group consisting of: primary alcohols; secondary alcohols; tertiary alcohols; and phenols; and
the first catalyst comprises a salt of magnesium or of a rare earth element.

19 Claims, No Drawings

(56) References Cited

U.S. PATENT DOCUMENTS

| | | |
|---|---|---|
| 2021/0214297 A1 | 7/2021 | Bleith et al. |
| 2021/0269393 A1 | 9/2021 | Treskow et al. |
| 2021/0332005 A1 | 10/2021 | Treskow et al. |
| 2022/0112154 A1 | 4/2022 | Treskow et al. |
| 2022/0281801 A1 | 9/2022 | Hartmann et al. |

FOREIGN PATENT DOCUMENTS

| | | |
|---|---|---|
| EP | 3 235 801 | 10/2017 |
| EP | 3248959 | 11/2017 |
| FR | 2739850 * | 4/1997 |
| JP | S58-131940 | 8/1983 |
| JP | H05-98031 | 4/1993 |
| JP | H06-199962 | 7/1994 |
| JP | H06-287241 | 10/1994 |
| JP | 1995 07 017940 * | 1/1995 |
| JP | H07-330847 | 12/1995 |
| JP | H10-226692 | 8/1998 |
| JP | H10-265312 | 10/1998 |
| JP | 2002-088018 * | 3/2002 |
| JP | 2003-176318 | 6/2003 |
| JP | 2007 091665 | 4/2007 |
| JP | 2007091665 * | 4/2012 |
| JP | 2014-098100 | 5/2014 |
| JP | 2014-111550 | 6/2014 |
| JP | 2014148386 | 8/2014 |
| JP | 2015186787 | 10/2015 |
| KR | 10-1855122 | 6/2018 |
| WO | WO 00/59982 | 10/2000 |
| WO | WO 2004/007418 | 1/2004 |
| WO | WO 2005/090281 | 9/2005 |
| WO | WO 2018/031373 | 2/2018 |

OTHER PUBLICATIONS

Examiner Interview Summary for copending U.S. Appl. No. 17/268,463, dated Nov. 9, 2022.
Non Final Office Action for copending U.S. Appl. No. 17/268,463, dated Dec. 1, 2022.
Notice of Withdrawal for copending U.S. Appl. No. 17/268,463, dated Dec. 5, 2022.
Amendment & Response to Non Final Office Action for copending U.S. Appl. No. 17/268,463, filed Mar. 1, 2023.
Clark, et al., "A One-Step Procedure for the Monoacylation of Symmetrical 1,2-Diols," *J. Org. Chem.* 67:5226-5231 (2002).
Amendment & Response to Final Office Action for copending U.S. Appl. No. 17/268,463, filed Jul. 10, 2023.
Request for Continued Examination for copending U.S. Appl. No. 17/268,463, filed Jul. 10, 2023.
Non Final Office Action for copending U.S. Appl. No. 17/268,463, dated Aug. 1, 2023.
Final Office Action for copending U.S. Appl. No. 17/268,463, dated Apr. 12, 2023.
Patil, et al., "Chemoselective Acylation of Amines, Alcohols and Phenols Using Magnesium Chloride Under Solvent Free Condition," *Int. J. Chem. Sci.* 13(1):450-458 (2015).
International Search Report for corresponding PCT/EP2019/070593, filed Jul. 31, 2019.
Written Opinion of the International Searching Authority for corresponding PCT/EP2019/070593, filed Jul. 31, 2019.
International Preliminary Report on Patentability for corresponding PCT/EP2019/070593, filed Jul. 31, 2019.
European Search Report for corresponding EP 18 18 9276, filed Aug. 16, 2018.
English language translation of an Office Action for corresponding Japanese application 2021-507789, drafted Apr. 20, 2022.
Ishihara, et al., "Scandium Trifluoromethanesulfonate as an Extremely Active Acylation Catalyst," *J. Am. Chem. Soc.* 117:4413-4414 (1995).
Pansare, et al., "Magnesium Bromide Catalysed Acylation of Alcohols," *Synethetic Comm.* 30(14):2587-2592 (2000).
Yoshinori Nakane, et al., "New crosslinking system using blocked carboxylic acid," *Progress in Organic Coating* 31:113-120 (1997).
U.S. Appl. No. 16/479,497, filed Jul. 19, 2019, US-2019/0352251 A1, Nov. 21, 2019, Hartmann.
U.S. Appl. No. 16/973,995, filed Dec. 10, 2020, US-2021/0163439 A1, Jun. 3, 2021, Treskow.
U.S. Appl. No. 17/057,659, filed Nov. 21, 2020, US-2021/0214297 A1, Jul. 15, 2021, Bleith.
U.S. Appl. No. 17/260,223, filed Jan. 14, 2021, US-2021/0332005 A1, Oct. 28, 2021, Treskow.
U.S. Appl. No. 17/260,226, filed Jan. 14, 2021, US-2021/0269393 A1, Sep. 2, 2021, Treskow.
U.S. Appl. No. 17/262,735, filed Jan. 24, 2021, US-2022/0112154 A1, Apr. 14, 2022, Treskow.
Kubala, "Magnesium Oxide: Benefits, Side Effects, Dosage, and Interactions," Nutrition, 15 pages, published 2021 (in copending U.S. Appl. No. 17/268,463).
Notice of Allowance for copending U.S. Appl. No. 17/268,463, dated Mar. 4, 2022.
Notice of Withdrawal for copending U.S. Appl. No. 17/268,463, dated Jun. 17, 2022.
Non Final Office Action for copending U.S. Appl. No. 17/268,463, dated Jul. 8, 2022.
Amendment & Response to Non Final Office Action for copending U.S. Appl. No. 17/268,463, filed Oct. 5, 2022.
U.S. Appl. No. 17/750,383, filed May 22, 2022, US-2022/0281801 A1, Hartmann.
Amendment & Response to Office Action for copending U.S. Appl. No. 17/268,463, filed Oct. 28, 2023.
Notice of Allowance for copending U.S. Appl. No. 17/268,463, dated Nov. 29, 2023.

* cited by examiner

PREPARATION OF (METH)ACRYLIC ACID ESTERS

CROSS REFERENCE TO RELATED APPLICATIONS

The present application is a continuation of U.S. Ser. No. 17/268,463, which is US national stage of international application PCT/EP2019/070593, which had an international filing date of Jul. 31, 2019 and which was published on Feb. 20, 2020. The PCT application claims priority to EP 18189276.1, filed on Aug. 16, 2018. The contents of these previous applications is hereby incorporated by reference in their entirety.

The invention relates to a method for preparation of (meth)acrylic acid esters from (meth)acrylic acid anhydrides.

(Meth)acrylic acid esters are commonly used as monomers for the preparation of various poly(meth)acrylates and the corresponding copolymers. Accordingly, a variety of methods of obtaining (meth)acrylic acid esters are known. These methods include, in particular, transesterification reactions in which methyl methacrylate is reacted with an alcohol. A further common possibility is an acylation of an alcohol with (meth)acrylic acid anhydride.

Acylation of alcohols with (meth)acrylic acid anhydrides, in particular with methacrylic acid anhydride is typically carried out in the presence of acids such as sulphuric acid. Under these conditions, undesired reactions such as polymerisation of the anhydrides commonly take place and therefore the product yields of the (meth)acrylic acid esters are only moderate. Additionally, preparation of (meth)acrylic acid esters of sterically hindered alcohols is known to suffer from low reaction yields, because such alcohols not only have a low reactivity towards (meth)acrylic acid anhydrides but also tend to undergo undesired dehydration under typically employed reaction conditions.

For these reasons, in order to achieve a reasonable conversion of sterically hindered alcohols and phenols, (meth)acrylic acid anhydrides are commonly used in a large excess. This is disadvantageous from economic and environmental points of view since (meth)acrylic acid anhydrides are rather expensive and recovery of the unreacted excess of the (meth)acrylic acid anhydride is difficult.

Historically, a considerable number of methods for acylation of alcohols with non-polymerizable anhydrides such as acetic acid anhydride has been developed. However, it is well-known that these methods typically fail with (meth)acrylic acid anhydrides, because the reactivity and chemical behaviour of the (meth)acrylic acid anhydrides differ significantly from those of acetic acid anhydride.

U.S. Pat. No. 4,540,743 A describes acylation of polyvinyl alcohols by esterifying these alcohols with an activated (meth)acrylic acid anhydride in the presence of a tertiary amine. This procedure requires a relatively large amount of a tertiary amine. As a consequence, said tertiary amine needs to be separated from the product mixture in a separate washing step which generates a considerable amount of aqueous waste.

In view of the above-described technical problems of the prior art it has been the purpose of the present invention, to develop a more efficient industrially applicable process for preparation of (meth)acrylic acid esters from (meth)acrylic acid anhydrides. Such process should ideally offer the following advantages:

high product yields of (meth)acrylic acid esters and high conversions
short reaction times
low excess of (meth)acrylic acid anhydride
low amounts of the acylation catalyst which, if desired, can be easily separated from the resulting product.

Additionally, the process should be suitable for preparation of di- or poly(meth)acrylates on an industrial scale in an efficient and inexpensive manner.

The present invention is based on a surprising finding that activation of (meth)acrylic acid anhydrides can be accomplished in a highly efficient way by using a salt of magnesium or of a rare earth element as a catalyst.

Accordingly, one aspect of the present invention relates to a process for preparation of a (meth)acrylic acid ester, the process comprising at least the following step (a):

(a) reaction between (meth)acrylic acid anhydride of Formula (I)

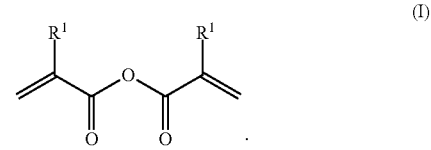

wherein $R^1$ is a hydrogen atom or a methyl group, and a substrate in the presence of a salt of magnesium or of a rare earth element, whereby a product mixture comprising the (meth)acrylic acid ester is formed.

The terms "(meth)acrylates" and "(meth)acrylic" as used herein may refer to acrylates and methacrylates. The (meth)acrylic acid anhydride of Formula (I) may be acrylic acid anhydride ($R^1$ is a hydrogen atom) or methacrylic acid anhydride ($R^1$ is a methyl group).

The first catalyst used in the step (a) catalyses the reaction between the (meth)acrylic acid anhydride of formula (I) and the substrate. According to the present invention, the first catalyst comprises a salt of magnesium or of a rare earth element.

The term "rare earth element" as used herein refers to an element selected from cerium, dysprosium, erbium, europium, gadolinium, holmium, lanthanum, lutetium, neodymium, praseodymium, promethium, samarium, scandium, terbium, thulium, ytterbium and yttrium. In a particularly preferred embodiment, the term "rare earth element" refers to an element selected from lanthanum, ytterbium, Yttrium and scandium.

In principle, substantially any salt of magnesium or of the above listed rare earth elements is suitable for use as the first catalyst in the present invention. However, the catalytic activity of the first catalyst is particularly high if the salt is selected from fluoride, chloride, bromide, iodide, acetate, sulphate, perchlorate and trifluoromethanesulfonate. In a particularly preferred embodiment, the salt may be selected from a chloride, bromide, iodide and trifluoromethanesulfonate.

Accordingly, the catalytic activity of the first catalyst is particularly high when the first catalyst comprises a halide of magnesium or of a rare earth element, a perchlorate of magnesium or of a rare earth element or a trifluoromethanesulfonate of magnesium or of a rare earth element. In particular, if the first catalyst is selected from the group consisting of magnesium bromide, magnesium iodide, magnesium chloride, magnesium bis-(trifluoromethylsulfonyl)- imid, magnesium perchlorate, lanthanum (III) trifluoromethanesulfonate, ytterbium (III) trifluoromethanesulfonate, yttrium (III) trifluoromethanesulfonate and scandium (III) trifluoromethanesulfonate product yields of the (meth)acrylic acid ester formed in the reaction step (a) are particularly high.

The first catalyst may be used in an anhydrous form or as a hydrate.

Remarkably, the reaction between the (meth)acrylic acid anhydride of Formula (I) and the substrate in the reaction step (a) proceeds smoothly even if the first catalyst is present in relatively low amounts. Nevertheless, by using the first catalyst in higher amounts, the reaction time during the reaction step (a) can be additionally reduced. Depending on the reactivity of the substrate, the total amount of the first catalyst in the step (a) is typically chosen to be between 0.001 mol.-% and 10 mol.-%, more preferably between 0.01 mol.-% and 1.0 mol.-%, even more preferably between 0.1 mol.-% and 0.5 mol.-%, based on the amount of the substrate.

The reaction solvent for the step (a) is not particularly limited, as long as the solvent cannot undergo a chemical reaction with the (meth)acrylic acid anhydride of Formula (I) and its boiling point allows the step (a) to be carried out at the desired temperature. Advantageously, however, the step (a) is carried out in the absence of any solvent.

The order of addition of reagents in the step (a) is not particularly limited, Thus, in one embodiment, the first catalyst is first dispersed in the substrate and, subsequently, the (meth)acrylic acid anhydride of Formula (I) is added thereto. Alternatively, the first catalyst may first be dispersed in the (meth)acrylic acid anhydride of Formula (I), followed by addition of the substrate to the resulting dispersion.

In some embodiments, it is also possible to prepare a mixture of the (meth)acrylic acid anhydride of Formula (I) with the substrate first and start the reaction by adding the first catalyst thereto. However, use of this procedure on an industrial scale is generally more difficult.

The optimal reaction temperature during the step (a) can be readily adjusted by a skilled person depending on the reactivity of the substrate and of the (meth)acrylic acid anhydride of Formula (I). Typically, the reaction temperature during the step (a) is kept between 20° C. and 140° C., preferably between 40° C. and 110° C., more preferably between 60° C. and 90° C.

Due to a high catalytic activity of the first catalyst, the reaction time for the step (a) typically ranges between 10 minutes and 10 hours, usually between 30 minutes and 4 hours. As will be readily appreciated by a skilled person, the reaction time for the step (a) can also be adjusted by varying the reaction temperature and the amount of the first catalyst.

The substrates suitable for use in the process of the present invention are not particularly limited and may be selected from substantially any primary alcohols, secondary alcohols, tertiary alcohols, and phenols. For instance, in one embodiment of the present invention the substrate may be selected from the group consisting of primary alcohols, secondary alcohols, tertiary alcohols having one or several hydroxyl groups and phenols. For instance, the substrate may be advantageously selected from primary alcohols, secondary alcohols and tertiary alcohols having one hydroxyl group. Use of these substrates smoothly leads to the corresponding (meth)acrylic acid monoesters in good chemical yields.

The molar ratio (meth)acrylic acid anhydride: substrate in the step (a) is not particularly limited and can be adjusted depending on the reactivity of the substrate and of the (meth)acrylic acid anhydride. For instance, the molar ratio (meth)acrylic acid anhydride: substrate in the step (a) may be selected to be between 5:1 and 1:5, preferably between 3:1 and 1:3, even more preferably between 2:1 and 1:2, yet even more preferably between 1.5:1 and 1:1.5.

The reaction between (meth)acrylic acid anhydride of Formula (I) and as substrate in the step (a) is often carried out in a presence of a slight excess of the (meth)acrylic acid anhydride, e.g. of at least 10 mol. % excess, or of at least 20 mol. % excess, based on the amount of the substrate, In order to separate the unreacted excess of the (meth)acrylic acid anhydride from the obtained (meth)acrylic acid ester, an auxiliary alcohol may be added to the product mixture obtained in the step (a). Under these conditions, a product mixture comprising the desired methacrylic acid ester and a methacrylic acid ester of the auxiliary alcohol is formed. Subsequently, the methacrylic add ester of the auxiliary alcohol can be separated from this product mixture, typically by distillation.

Hence, in this embodiment, the process of the present invention can be carried out as follows:

(a) reaction between (meth)acrylic add anhydride of Formula (I) and a substrate in the presence of a first catalyst, whereby a product mixture comprising the (rneth)acrylic add ester is formed;

(b) addition of an auxiliary alcohol to the product mixture obtained in the step (a), whereby a product mixture comprising the (meth)acrylic acid ester and a (meth)acrylic acid ester of the auxiliary alcohol is formed; and (c) removal of the (meth)acrylic acid ester of the auxiliary alcohol from the product mixture obtained in the step (b).

The auxiliary alcohol is usually a primary or a secondary alcohol. Since the auxiliary alcohol has a high reactivity, it smoothly reacts with the unreacted (meth)acrylic add anhydride of Formula (I) after the step (a) thereby forming a (meth)acrylic acid ester of the auxiliary alcohol. For the sake of an easy separation of the (meth)acrylic acid ester of the auxiliary alcohol in process step (c) by distillation, it is preferred that the auxiliary alcohol has a boiling point of not more than 150° C., preferably not more than 120° C., more preferably not more than 80° C., measured at a pressure of $10^5$ Pa. For instance, the auxiliary alcohol can be advantageously selected from methanol, ethanol, n-propanol, isopropanol or a mixture thereof, wherein methanol is particularly preferred.

Finally, a further aspect of the present invention is use of a salt of magnesium or of a rare earth element as a catalyst in a reaction between (meth)acrylic acid anhydride of Formula (I)

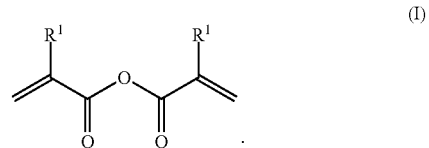

wherein $R^1$ is a hydrogen atom or a methyl group;
and a substrate, the reaction yielding a product mixture comprising a (meth)acrylic acid ester,
wherein
the substrate is selected from the group consisting of primary alcohols, secondary alcohols, tertiary alcohols and phenols.

In the following, the present invention will be illustrated by examples which are, however, are not meant to be limiting in any way.

Examples

Examples 1-82: Evaluation of Catalytic Activity of the First Catalyst

As a benchmark reaction for evaluation of the catalytic activity of the first catalyst, acylation of menthol by methacrylic anhydride was investigated.

Preparation of A Stock Solution of Menthol and Methacrylic Anhydride 156 g (1.0 mol) of natural menthol and 161.9 g (1.05 mol) of methacrylic anhydride, stabilized with 2000 ppm of 2.4-dimethyl-6-tert-butylphenol and 1000 ppm of hydroquinone monomethyl ether and 10 ppm of 4-hydroxy-2,2,6,6-tetramethylpiperidinooxyl (ppm based on the total mass of anhydride and alcohol) were combined. The obtained mixture was gently heated in the absence of any catalyst and a clear stock solution was obtained.

General Procedure or Examples 1-67:

7.0 g samples of the stock solution were placed in a 15 mL pressure tube with a Teflon® plug and a magnetic agitator. To this solution, 0.1 mol % (unless indicated otherwise), based on the menthol, of the first catalyst were added and the pressure tube was tightly closed. Subsequently, the pressure tubes were placed for 3 h in an oil bath at 50° C. with an integrated magnetic stirrer and stirred.

A sample without any catalyst (Example 35) in the oil bath at 50° C. served as a reference sample, a further sample of the stock solution was kept at room temperature as a reaction control. After 3 hours, the conversion and the product yield were determined by gas chromatography (area-%).

The results of Examples 1-67 are summarised in Table 1 below:

TABLE 1

Evaluation of catalytic activity of the first catalyst with methacrylic acid anhydride

| Example | First catalyst | Conversion (area-%, GC) | Product yield (area-%, GC) |
| --- | --- | --- | --- |
| 1 | magnesium bromide, anhydrous | 59.1 | 45.1 |
| 2 | magnesium bromide, hydrate | 58.9 | 45.0 |
| 3 | ytterbium (III) triflate, hydrate | 57.7 | 44.2 |
| 4 | dysprosium (III) perchlorate hexahydrate, 50 wt.-% in water | 56.8 | 41.5 |
| 5 | magnesium-bis-(trifluoromethylsulfonylimide) | 46.3 | 36.7 |
| 6 | scandium (III) triflate | 44.7 | 29.5 |
| 7 | magnesium iodide, anhydrous | 40.0 | 30.9 |
| 8 | europium (III) perchlorate 50 wt.-% in water | 39.8 | 28.3 |
| 9 | ytterbium (III) perchlorate 50 wt.-% in water | 39.0 | 27.1 |
| 10 | magnesium perchlorate, anhydrous | 35.4 | 25.5 |
| 11 | magnesium chloride, anhydrous | 35.0 | 24.6 |
| 12 | magnesium nitrate, hexahydrate | 26.6 | 18.4 |
| 13 | manganese (II) perchlorate, hexahydrate | 22.3 | 15.5 |
| 14 | magnesium acetate, tetrahydrate | 19.1 | 10.1 |
| 15 | lanthanum (III) triflate, anhydrous | 19.0 | 13.0 |
| 16 | bismuth (III) triflate | 18.9 | 12.5 |
| 17 | 4-dimethylaminopyridine (2.0 mol %) | 18.6 | 12.2 |
| 18 | zinc perchlorate, hexahydrate | 18.0 | 12.2 |
| 19 | magnesium acetylacetonate, anhydrous | 17.2 | 11.8 |
| 20 | magnesium methacrylate | 16.6 | 10.4 |

TABLE 1-continued

Evaluation of catalytic activity of the first catalyst with methacrylic acid anhydride

| Example | First catalyst | Conversion (area-%, GC) | Product yield (area-%, GC) |
| --- | --- | --- | --- |
| 21 | magnesium acrylate | 16.0 | 10.6 |
| 22 | benzyltriethylammonium chloride | 13.4 | 1.3 |
| 23 | tin (II) chloride, dihydrate | 12.8 | 7.8 |
| 24 | iron (III) perchlorate, hydrate (violet) | 12.3 | 7.8 |
| 25 | aluminium perchlorate, nonahydrate | 12.3 | 7.6 |
| 26 | indium (III) perchlorate, octahydrate | 11.9 | 7.4 |
| 27 | Dowex ® M31 (1.0 mol.-%) | 11.5 | 4.0 |
| 28 | gallium (III) perchlorate, hydrate | 11.4 | 6.9 |
| 29 | cadmium perchlorate, hexahydrate | 9.9 | 4.7 |
| 30 | iron (III) perchlorate, hydrate (yellow) | 9.9 | 5.7 |
| 31 | trimethylsilyl triflate | 9.3 | 5.4 |
| 32 | calcium chloride | 8.8 | 4.2 |
| 33 | Dowex ® M31 (0.1 mol.-%) | 8.0 | 1.9 |
| 34 | zinc acetate, anhydrous | 7.9 | 3.4 |
| 35 | no catalyst | 7.2 | 0.8 |
| 36 | 1.4-bis(hexafluoro-α-hydroxyisopropyl) benzene, hydrate | 6.4 | 1.5 |
| 37 | 4-dimethylaminopyridine | 6.4 | 2.6 |
| 38 | silver perchlorate, monohydrate | 5.0 | 0.8 |
| 39 | zeolite (aluminium silicate) | 6.3 | 1.1 |
| 40 | magnesium triflate (0.1 mol %) + tetramethylammonium bromide (0.2 mol %) | 6.2 | 4.3 |
| 41 | N,N'-diphenylthiourea | 6.0 | 1.8 |
| 42 | sodium methacrylate | 5.9 | 3.3 |
| 43 | lithium perchlorate, trihydrate | 5.8 | 0.9 |
| 44 | cobalt (II) chloride, anhydrous | 5.7 | 2.3 |
| 45 | sulfuric acid | 5.6 | 5.1 |
| 46 | sodium perchlorate, anhydrous | 5.6 | 0.8 |
| 47 | tetramethylammonium bromide | 5.5 | 1.1 |
| 48 | calcium perchlorate, hydrate | 5.3 | 1.3 |
| 49 | magnesium carbonate | 5.3 | 1.1 |
| 50 | 4-methylaminopyridine | 5.1 | 2.2 |
| 51 | silver perchlorate, monohydrate | 5.0 | 0.8 |
| 52 | barium perchlorate, trihydrate | 4.7 | 0.8 |
| 53 | methanesulfonic acid | 4.6 | 2.4 |
| 54 | rubidium perchlorate, anhydrous | 4.6 | 0.8 |
| 55 | potassium perchlorate | 4.5 | 0.7 |
| 56 | zinc bromide, anhydrous | 4.5 | 1.6 |
| 57 | cesium perchlorate | 4.5 | 0.7 |
| 58 | magnesium triflate | 4.4 | 2.2 |
| 59 | barium chloride, dihydrate | 4.4 | 1.4 |
| 60 | magnesium sulphate, anhydrous | 4.3 | 1.4 |
| 61 | magnesium sulphate, hydrate | 3.9 | 0.7 |
| 62 | magnesium hydrogenphosphate, trihydrate | 3.4 | 1.3 |
| 63 | magnesium triflate | 3.3 | 1.2 |
| 64 | zinc (II) chloride | 3.2 | 1.7 |
| 65 | sodium iodide | 2.8 | 1.0 |
| 66 | tetramethylammonium bromide (0.2 mol %) | 2.6 | 0.8 |
| 67 | potassium triflate | 2.4 | 1.1 |

The data presented in Table 1 show that various catalysts (Lewis acids, Brønsted acids, tertiary amines), which are commonly employed for acylation of alcohols with acetic acid anhydride, are not suitable for use with (meth)acrylic acid anhydrides. Under the tested reaction conditions, use of these catalysts led to a conversion of not more than 18%.

Surprisingly, salts of magnesium and of a rare earth element showed a significantly higher catalytic activity under the same reaction conditions.

The data in Table 1 further show that also the nature of the anion has a strong effect on the catalytic activity of the tested salts. Contrary to expectations of the inventors, no correlation between the Lewis acid strength of the anions of the tested salts and their catalytic activity was found. Magnesium halogenides and trifluoromethanesulfones of rare earth metals surprisingly showed the highest catalytic activity in acylation with (meth) acrylic acid anhydrides. Perchlorates of the above metals also showed a good catalytic activity.

Reference Examples 66-76: Evaluation of Catalytic Activity of the First Catalyst As reference examples for evaluation of the catalytic activity of the first catalyst, acylation of menthol by acetic acid anhydride was investigated.

Preparation of A Stock Solution of Menthol and Methacrylic Anhydride 37.8 g (0.17 mol) of natural menthol and 161.9 g (0.1785 mol) of acetic acid anhydride were combined. The obtained mixture was gently heated in the absence of any catalyst and a clear stock solution was obtained.

General Procedure for Examples 68-76

7 g samples of the stock solution were placed in a 15 mL pressure tube with a Teflon® plug and a magnetic agitator. To this solution, 0.1 mol% (unless indicated otherwise), based on the menthol, of the first catalyst were added and the pressure tube was tightly closed. Subsequently, the pressure tubes were placed for 3 h in an oil bath at 50° C. (unless indicated otherwise) with an integrated magnetic stirrer and stirred.

After 3 hours, the contents of acetic acid, acetic acid anhydride, menthol and of the product were determined by gas chromatography (area-%). Based on these data, the reaction conversion, based on the acetic add anhydride and on the menthol was calculated.

The results of Examples 68-76 are summarised in Table 2 below:

2.4-dimethyl-6-teat-butylphenol and 1000 ppm of hydroquinone monomethyl ether and 10 ppm of 4-hydroxy-2,2,6,6-tetramethylpiperidinooxyl (ppm based on the total mass of anhydride and alcohol) were combined. The obtained mixture was gently heated in the absence of any catalyst and a clear stock solution was obtained.

General Procedure for Example 77-95:

7.0 g samples of the stock solution were placed in a 15 mL pressure tube with a Teflon® plug and a magnetic agitator. To this solution, 0.1 mol % (unless indicated otherwise), based on the menthol, of the first catalyst were added and the pressure tube was tightly closed. Subsequently, the pressure tubes were placed for 3 h in an oil bath at 90° C. with an integrated magnetic stirrer and stirred.

A sample without any catalyst (Example 93) in the oil bath at 90°C. served as a reference sample. After 3 hours, the conversion and the product yield were determined by gas chromatography (area-%).

The results of Examples 77-95 are summarised in Table 3 below:

TABLE 3

Evaluation of catalytic activity of the first catalyst with methacrylic acid anhydride at 90° C.

| Example | First catalyst | Conversion (area-%, GC) | Product yield (area-%, GC) |
| --- | --- | --- | --- |
| 77 | lanthanum (III) perchlorate, hexahydrate | 99.10 | 78.2 |
| 78 | lanthanum (III) triflate, hydrate | 98.50 | 78.5 |
| 79 | lanthanum (III) triflate, anhydrous | 97.90 | 79.0 |

TABLE 2

Evaluation of catalytic activity of the first catalyst with acetic acid anhydride

| Example | First catalyst | AcOH (area-%, GC) | Ac₂O (area-%, GC) | Menthol (area-%, GC) | Product (area-%, GC) | Conversion Ac₂O (area-%, GC) | Conversion menthol (area-%, GC) |
| --- | --- | --- | --- | --- | --- | --- | --- |
| 68 | no catalyst, before reaction start | 0.0 | 17.42 | 81.89 | 0.0 | 0.0 | 0.0 |
| 69 | no catalyst, 3 h at 23° C. | 0.0 | 17.01 | 80.82 | 0.0 | 2.30 | 1.30 |
| 70 | no catalyst, 3 h at 50° C. | 0.98 | 15.51 | 71.98 | 11.15 | 11.00 | 12.10 |
| 71 | magnesium bromide, anhydrous | 7.38 | 2.02 | 7.7 | 82.48 | 88.40 | 90.60 |
| 72 | ytlerbium (III) triflate, hydrate | 8.31 | 0.29 | 0.03 | 90.98 | 98.40 | 100.00 |
| 73 | scandium triflate | 8.24 | 0.25 | 0.02 | 91.1 | 98.60 | 100.00 |
| 74 | lanthanum (III) triflate | 7.82 | 0.3 | 0.0 | 91.53 | 98.30 | 100.00 |
| 75 | zinc perchlorate, hexahydrate | 7.35 | 0.30 | 0.0 | 91.96 | 98.30 | 100.0 |
| 76 | 4-dimethylaminopyridine, 2 mol.-% | 7.43 | 0.7 | 1.28 | 90.6 | 96.00 | 98.40 |

The data in Table 2 confirm that commonly employed acylation catalysts such as 4- dimethylaminopyridine show an excellent catalytic activity with acetic acid anhydride. However, these catalysts surprisingly fail when used with methacrylic acid anhydride (cf. Table 1 above). This shows that common general knowledge on the catalytic behaviour of typical acylation catalysts is not applicable to acylation with (meth)acrylic acid anhydrides.

Examples 77-95: Evaluation of Catalytic Activity of the First Catalyst at 90° C.

As a benchmark reaction for evaluation of the catalytic activity of the first catalyst, acylation of menthol by methacrylic anhydride at 90° C. was investigated.

Preparation of A Stock Solution of Menthol and Methacrvlic Anhydride 156 g (1.0 mol) of natural menthol and 161.9 g (1.05 mol) of methacrylic anhydride, stabilized with 2000 ppm of TABLE 3-continued Evaluation of catalytic activity of the first catalyst with methacrylic acid anhydride at 90° C.

| Example | First catalyst | Conversion (area-%, GC) | Product yield (area-%, GC) |
| --- | --- | --- | --- |
| 80 | lanthanum (III) bromide, heptahydrate | 77.60 | 59.2 |
| 81 | magnesium bromide, hexahydrate | 77.00 | 60.5 |
| 82 | magnesium bromide | 75.00 | 61.0 |
| 83 | lanthanum (III) chloride, heptahydrate | 67.40 | 50.8 |
| 84 | lanthanum (III) methacrylate | 66.20 | 49.2 |
| 85 | lanthanum (III) nitrate, hexahydrate | 65.00 | 48.5 |
| 86 | lanthanum (III) nitrate | 62.90 | 47.3 |
| 87 | lanthanum (III) acetate, hydrate | 62.80 | 48.4 |

TABLE 3-continued

Evaluation of catalytic activity of the first catalyst with methacrylic acid anhydride at 90° C.

| Example | First catalyst | Conversion (area-%, GC) | Product yield (area-%, GC) |
|---|---|---|---|
| 88 | lanthanum (III) acetylacetonate, hydrate | 62.80 | 48.7 |
| 89 | lanthanum (III) chloride, hexahydrate | 57.90 | 44.8 |
| 90 | lanthanum (III) methanesulfonate | 54.70 | 41.5 |
| 91 | lanthanum (III) sulphate, hydrate | 40.20 | 28.4 |
| 92 | lanthanum (III) phosphate, hydrate | 40.20 | 28.3 |
| 93 | no catalyst | 38.90 | 28.7 |
| 94 | zinc chloride | 38.90 | 30.0 |
| 95 | lanthanum (III) oxalate, decahydrate | 38.50 | 28.7 |

Experimental data in Table 3 confirm that lanthanum (III) salts have an excellent catalytic activity at 90° C. which is even higher than the catalytic activity of magnesium bromide at this temperature. The data further illustrate that the catalysts may be employed both as anhydrous salts and as hydrates without any noticeable loss of catalytic activity.

The conversion in the Reference Example 93 i.e. in the absence of any catalyst was 38.90%. Remarkably, use of strong Lewis acids such as zinc chloride (cf. Example 94) brought no improvements beyond the conversion level of 38.90%.

Examples 96-103: Evaluation of Catalytic Activity of the First Catalyst With Glycerin Carbonate As a benchmark reaction for evaluation of the catalytic activity of the first catalyst, acylation of glycerin carbonate by methacrylic anhydride at 80° C. was investigated.

Preparation of A Stock Solution of Glycerin Carbonate and Methacrylic Anhydride 118 g (1.0 mol) of glycerin carbonate and 162.0 g (1.05 mol) of methacrylic anhydride, stabilized with 2000 ppm of 2.4-dimethyl-6-tert-butylphenol and 1000 ppm of hydroquinone monornethyl ether and 10 ppm of 4-hydroxy-2,2,6,6-tetramethylpiperidinooxyl (ppm based on the total mass of anhydride and alcohol) were combined. The obtained mixture was gently heated in the absence of any catalyst and a dear stock solution was obtained.

General Procedure for Example 96-103:

7.0 g samples of the stock solution were placed in a 15 mL pressure tube with a Teflon® plug and a magnetic agitator. To this solution, 0.1 mol % (unless indicated otherwise), based on the glycerin carbonate, of the first catalyst were added and the pressure tube was tightly closed. Subsequently, the pressure tubes were placed for 6 h in an oil bath at 80° C. with an integrated magnetic stirrer and stirred.

A sample without any catalyst (Example 96) in the oil bath at 80° C. served as a reference sample. After 6 hours, the conversion and the product yield were determined by gas chromatography (area-%).

The results of Examples 96-103 are summarised in Table 4 below:

TABLE 4

Evaluation of catalytic activity of the first catalyst with methacrylic acid anhydride and glycerin carbonate at 80° C.

| Example | First catalyst | Conversion (area-%, GC) | Product yield (area-%, GC) |
|---|---|---|---|
| 96 | no catalyst | 6.00% | 13.90% |
| 97 | magnesium bromide | 37.50% | 27.90% |
| 98 | magnesium chloride | 45.70% | 31.60% |
| 99 | zinc perchlorate, hexahydrate | polymer formation | — |
| 100 | 4-dimethylaminopyridine | 3.70% | 15.30% |
| 101 | lanthanium (III) triflate | 91.30% | 48.40% |
| 102 | sulfuric acid, 1.0 mol.-% | polymer formation | — |
| 103 | zinc chloride | 0.40% | 10.30% |

The results in Table 4 show that in the absence of any catalyst (Reference Example 96) the conversion was as low as 6.00%. Use of known acylation catalysts such as 4-dimethyl-aminopyridine (Example 100) and zinc chloride (Example 103) failed to bring any improvements. On the contrary, the product conversion in these examples was even lower than in the absence of any catalyst.

In the presence of zinc perchlorate (Reference Example 99) or sulphuric acid (Reference Example 102) an undesired polymer formation took place. Thus, no desired product could be detected.

Finally, use of the catalysts according to the present invention allowed preparation of the desired product in moderate to excellent yields.

Examples 104-111: Evaluation of Catalytic Activity of the First Catalyst With Isopropanol As a benchmark reaction for evaluation of the catalytic activity of the first catalyst, acylation of isopropanol by methacrylic anhydride at 90° C. was investigated.

Preparation of A Stock Solution of Isopropanol and Methacrylic Anhydride 30.1 g (0.50 mol) of isopropanol and 108.0 g (0.7 mol) of methacrylic anhydride, stabilized with 2000 ppm of 2.4-dimethyl-6-tert-butylphenol and 1000 ppm of hydroquinone monomethyl ether and 10 ppm of 4-hydroxy-2,2,6,6-tetramethylpiperidinooxyl (ppm based on the total mass of anhydride and alcohol) were combined. The obtained mixture was gently heated in the absence of any catalyst and a clear stock solution was obtained.

General Procedure or Example 104-111:

7.0 g samples of the stock solution were placed in a 15 mL pressure tube with a Teflon® plug and a magnetic agitator. To this solution, 0.1 mol % (unless indicated otherwise), based on the isopropanol, of the first catalyst were added and the pressure tube was tightly closed.

Subsequently, the pressure tubes were placed for 6 h in an oil bath at 90° C. with an integrated magnetic stirrer and stirred.

A sample without any catalyst (Example 104) in the oil bath at 90° C. served as a reference sample. After 6 hours, the conversion and the product yield were determined by gas chromatography (area-%).

The results of Examples 104-111 are summarised in Table 5 below:

TABLE 5

Evaluation of catalytic activity of the first catalyst with methacrylic acid anhydride and isopropanol at 90° C.

| Example | First catalyst | Conversion (area-%, GC) | Product yield (area-%, GC) |
|---|---|---|---|
| 104 | no catalyst | 46.60% | 39.80% |
| 105 | magnesium bromide | 66.00% | 53.00% |
| 106 | magnesium perchlorate | 68.40% | 53.40% |
| 107 | magnesium chloride | 66.40% | 51.90% |
| 108 | zinc perchlorate, hexahydrate | polymer formation | — |
| 109 | 4-dimethylaminopyridine (2.0 mol.-%) | 59.90% | 44.80% |
| 110 | sodium methacrylate | 52.20% | 42.70% |
| 111 | zeolite | 47.90% | 42.20% |

The results in Table 5 show that in the absence of any catalyst (Reference Example 104) the conversion was 46.60%. Use of a known acylation catalyst 4-dimethylaminopyridine (Reference Example 109) brought only moderate improvements.

In the presence of zinc perchlorate (Reference Example 108) an undesired polymer formation took place and no desired product could be detected.

Examples 112-119: Evaluation Of Catalytic Activity Of The First Catalyst With Hexafluoroisopropanol As a benchmark reaction for evaluation of the catalytic activity of the first catalyst, acylation of hexafluoroisopropanol by methacrylic anhydride at 90° C. was investigated.

Preparation Of A Stock Solution Of Hexafluoroisopropanol And Methacrviic Anhydride 50.4 g (0.30 mol) of hexafluoroisopropanol and 64.8 g (0.42 mol) of methacrylic anhydride, stabilized with 2000 ppm of 2.4-dimethyl-6-tert-butylphenol and 1000 ppm of hydroquinone monomethyl ether and 10 ppm of 4-hydroxy-2.2.6.6-tetramethylpiperidinooxyl (ppm based on the total mass of anhydride and alcohol) were combined. The obtained mixture was gently heated in the absence of any catalyst and a clear stock solution was obtained.

General Procedure for Example 112-119:

7.0 g samples of the stock solution were placed in a 15 pressure tube with a Teflon® plug and a magnetic agitator. To this solution, 0.1 mol % (unless indicated otherwise), based on the hexafluoroisopropanol, of the first catalyst were added and the pressure tube was tightly closed. Subsequently, the pressure tubes were placed for 6 h in an oil bath at 90° C. with an integrated magnetic stirrer and stirred.

A sample without any catalyst (Reference Example 112) in the oil bath at 90° C. served as a reference sample. After 6 hours, the conversion and the product yield were determined by gas chromatography (area-%).

The results of Examples 112-119 are summarised in Table 6 below:

TABLE 6

Evaluation of catalytic activity of the first catalyst with methacrylic acid anhydride and hexafluoroisopropanol at 90° C.

| Example | First catalyst | Conversion (area-%, GC) | Product yield (area-%, GC) |
|---|---|---|---|
| 112 | no catalyst | 43.80% | 34.30% |
| 113 | Dowex ® M31 | polymer formation | — |

TABLE 6-continued

Evaluation of catalytic activity of the first catalyst with methacrylic acid anhydride and hexafluoroisopropanol at 90° C.

| Example | First catalyst | Conversion (area-%, GC) | Product yield (area-%, GC) |
|---|---|---|---|
| 114 | magnesium bromide | 67.10% | 20.10% |
| 115 | magnesium chloride | 67.70% | 19.70% |
| 116 | zinc perchlorate, hexahydrate | polymer formation | — |
| 117 | 4-dimethylaminopyridine (2.0 mol.-%) | 100.00% | 0.00% |
| 118 | sodium methacrylate | 45.40% | 33.30% |
| 119 | Zeolite | 44.90% | 33.60% |

The results in Table 6 show that in the absence of any catalyst (Reference Example 112) the conversion was 43.80%.

In the presence of zinc perchlorate (Reference Example 116) and Dowex® M31 (Reference Example 113) an undesired polymer formation took place and no desired product could be detected.

Examples 120.127: Evaluation Of Catalytic Activity Of The First Catalyst With Tert-Butanol As a benchmark reaction for evaluation of the catalytic activity of the first catalyst, acylation of tert-butanol by methacrylic anhydride at 90° C. was investigated.

Preparation Of A Stock Solution Of Tert-Butanol And Methacrylic Anhydride 37.1 g (0.50 mol) of tent-butanol and 107.9 g (0.70 mol) of methacrylic anhydride, stabilized with 2000 ppm of 2,4-dimethyl-6-tert-butylphenol and 1000 ppm of hydroquinone monomethyl ether and 10 ppm of 4-hydroxy-2,2,6,6-tetramethylpiperidinooxyl (ppm based on the total mass of anhydride and alcohol) were combined. The obtained mixture was gently heated in the absence of any catalyst and a clear stock solution was obtained.

General Procedure for Example 137-127:

7.0 g samples of the stock solution were placed in a 15 mL pressure tube with a Teflon® plug and a magnetic agitator. To this solution, 0.1 mol % (unless indicated otherwise), based on the tert.-butanol, of the first catalyst were added and the pressure tube was tightly closed. Subsequently, the pressure tubes were placed for 6 h in an oil bath at 90° C. with an integrated magnetic stirrer and stirred.

A sample without any catalyst (Reference Example 120) in the oil bath at 90° C. served as a reference sample. After 6 hours, the conversion and the product yield were determined by gas chromatography (area-%).

The results of Examples 120-127 are summarised in Table 7 below:

TABLE 7

Evaluation of catalytic activity of the first catalyst with methacrylic acid anhydride and tert.-butanol at 90° C.

| Example | First catalyst | Conversion (area- %, GC) | Product yield (area- %, GC) |
|---|---|---|---|
| 120 | no catalyst | 7.50 | 56.40 |
| 121 | Dowex ® M31 | polymer formation | — |
| 122 | magnesium bromide | 24.40 | 46.10 |
| 123 | magnesium perchlorate | 72.00 | 17.10 |
| 124 | zinc perchlorate, hexahydrate | polymer formation | — |
| 125 | 4-dimethylaminopyridine (2.0 mol.- %) | 17.40 | 50.40 |

TABLE 7-continued

Evaluation of catalytic activity of the first catalyst with methacrylic acid anhydride and tert.-butanol at 90° C.

| Example | First catalyst | Conversion (area-%, GC) | Product yield (area-%, GC) |
|---|---|---|---|
| 126 | sodium methacrylate | 4.50 | 58.20 |
| 127 | zeolite | 5.50 | 57.60 |

The results in Table 7 show that in the absence of any catalyst (Reference Example 120) the conversion was as low as 7.50%.

In the presence of zinc perchlorate (Reference Example 124) and Dowex® M31 (Reference Example 121) an undesired polymer formation took place. Thus, no desired product could be detected.

Use of magnesium bromide (Example 122) and of magnesium perchlorate (Example 123) i.e. of the catalysts according to the present invention allowed a significant yield improvement.

Examples 128-137: Evaluation Of Catalytic Activity Of The First Catalyst With 4-Hydroxybenzophenone As a benchmark reaction for evaluation of the catalytic activity of the first catalyst, acylation of 4-hydroxybenzophenone by methacrylic anhydride at 90° C. was investigated.

Preparation Of A Stock Solution Of 4-Hydroxybenzophenone And Methacrylic Anhydride 3.35 g (0.017 mol) of 4-hydroxybenzophenone and 3.65 g (0.024 mol) of methacrylic anhydride, stabilized with 2000 ppm of 2.4-dimethyl-6-tert-butylphenol and 1000 ppm of hydroquinone monomethyl ether and 10 ppm of 4-hydroxy-2.2.6.6-tetramethylpiperidinooxyl (ppm based on the total mass of anhydride and alcohol) were combined. The obtained mixture was gently heated in the absence of any catalyst and a clear stock solution was obtained.

General Procedure for Example 128-137:

7.0 g samples of the stock solution were placed in a 15 mL pressure tube with a Teflon® plug and a magnetic agitator. To this solution, 0.1 mol% (unless indicated otherwise), based on the tert-butanol, of the first catalyst were added and the pressure tube was tightly closed. Subsequently, the pressure tubes were placed for 6 h in an oil bath at 90° C. with an integrated magnetic stirrer and stirred.

A sample without any catalyst (Reference Example 128) in the oil bath at 90° C. served as a reference sample. After 6 hours, the conversion and the product yield were determined by gas chromatography (area-%).

The results of Examples 128-137 are summarised in Table 8 below:

TABLE 8

Evaluation of catalytic activity of the first catalyst with methacrylic acid anhydride 4-hydroxybenzophenone at 90° C.

| Example | First catalyst | Conversion (area-%, GC) | Product yield (area-%, GC) |
|---|---|---|---|
| 128 | no catalyst | 30.90% | 26.30% |
| 129 | ytterbium (III) triflate, hydrate | 83.60% | 73.30% |
| 130 | magnesium bromide | 70.00% | 62.20% |
| 131 | magnesium perchlorate | 67.90% | 61.90% |
| 132 | magnesium chloride | 70.20% | 66.10% |
| 133 | zinc perchlorate, hexahydrate | polymer formation | — |
| 134 | 4-dimethylaminopyridine (2,0 mol.-%) | 76.00% | 70.10% |
| 135 | sodium methacrylate | 60.60% | 57.70% |
| 136 | zeolite | 37.70% | 33.70% |
| 137 | lanthanum (III) triflate | 70.60% | 63.60% |

The results in Table 8 show that in the absence of any catalyst (Reference Example 128) the conversion was 30.9%.

In the presence of zinc perchlorate (Reference Example 133) an undesired polymer formation took place. Thus, no desired product could be detected.

Use of various catalysts according to the present invention allowed a significant yield improvement.

Examples 138-155: Catalytic Activity Of Different Amounts Of The First Catalyst

As a benchmark reaction for evaluation of the catalytic activity of different amounts of the first catalyst, acylation of menthol by methacrylic anhydride at 90° C. was investigated.

Preparation Of A Stock Solution Of Menthol And Methacrylic Anhydride 78.1 g (0.50 mol) of natural menthol and 107.9 g (0.70 mol) of methacrylic anhydride, stabilized with 2000 ppm of 2,4-dimethyl-6-tert-butylphenol and 1000 ppm of hydroquinone monomethyl ether and 10 ppm of 4-hydroxy-2,2,6,6-tetramethylpiperidinooxyl (ppm based on the total mass of anhydride and alcohol) were combined. The obtained mixture was gently heated in the absence of any catalyst and a clear stock solution was obtained.

General Procedure for Example 138-155:

7.0 g samples of the stock solution were placed in a 15 mL pressure tube with a Teflon® plug and a magnetic agitator. To this solution, the first catalyst was added and the pressure tube was tightly closed. Subsequently, the pressure tubes were in an oil bath at 90° C. with an integrated magnetic stirrer and stirred.

A sample without any catalyst (Reference Example 138) in the oil bath at 90° C. served as a reference sample. After the time periods indicated in Table 9, the conversion and the product yield were determined by gas chromatography (area-%).

The results of Examples 138-155 are summarised in Table 9 below:

TABLE 9

Evaluation of catalytic activity of the first catalyst with methacrylic acid anhydride and menthol at 90° C.

| Example | First catalyst | Reaction time (h) | First catalyst content (mol %) | Product yield (area-%, GC) |
|---|---|---|---|---|
| 138 | magnesium bromide, hydrate | 2 h | — | 8.40% |
| 139 | magnesium bromide, hydrate | 2 h | 0.05 | 15.10% |
| 140 | magnesium bromide, hydrate | 2 h | 0.1 | 20.80% |
| 141 | magnesium bromide, hydrate | 2 h | 0.2 | 25.50% |
| 142 | magnesium bromide, hydrate | 2 h | 0.5 | 29.60% |
| 143 | magnesium bromide, hydrate | 2 h | 1.0 | 33.00% |
| 144 | magnesium bromide, hydrate | 2 h | 5.0 | 40.00% |
| 145 | magnesium bromide, hydrate | 4 h | — | 13.90% |
| 146 | magnesium bromide, hydrate | 4 h | 0.05 | 24.90% |
| 147 | magnesium bromide, hydrate | 4 h | 0.1 | 29.80% |

TABLE 9-continued

Evaluation of catalytic activity of the first catalyst with
methacrylic acid anhydride and menthol at 90° C.

| Example | First catalyst | Reaction time (h) | First catalyst content (mol %) | Product yield (area-%, GC) |
|---|---|---|---|---|
| 148 | magnesium bromide, hydrate | 4 h | 0.2 | 32.80% |
| 149 | magnesium bromide, hydrate | 4 h | 0.5 | 37.80% |
| 150 | magnesium bromide, hydrate | 4 h | 1.0 | 41.90% |
| 151 | magnesium bromide, hydrate | 4 h | 5.0 | 47.30% |
| 152 | magnesium bromide, hydrate | 6 h | 0.1 | 35.20% |
| 153 | magnesium bromide, hydrate | 6 h | 0.25 | 37.80% |
| 154 | lanthanum (III) triflate | 6 h | 0.1 | 39.00% |
| 155 | lanthanum (III) triflate | 6 h | 0.25 | 45.70% |

The data in Table 9 show that the optimal amount of the first catalyst is typically between ca. 0.1 mol.-% and ca. 0.5 mol.-%, based on the amount of the substrate.

The invention claimed is:

1. A process for the preparation of a (meth)acrylic acid ester, comprising at least step (a) as follows:
(a) reacting a (meth)acrylic acid anhydride of Formula (I):

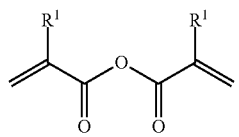

wherein $R^1$ is a hydrogen atom or a methyl group;
with a substrate in the presence of a first catalyst to form a product mixture comprising the (meth)acrylic acid ester; and wherein:
the substrate is a primary alcohol having one hydroxyl group; and
the first catalyst comprises a halide of magnesium;
wherein the temperature during step (a) is kept between 60° C. and 90° C.

2. The process of claim 1, wherein the first catalyst is selected from the group consisting of: magnesium bromide; magnesium iodide; and magnesium chloride.

3. The process of claim 1, wherein the total amount of the first catalyst in step (a) is between 0.001 mol.-% and 10 mol.-% based on the amount of the substrate.

4. The process of claim 1, wherein the total amount of the first catalyst in step (a) is between 0.01 mol.-% and 1.0 mol.-%, based on the amount of the substrate.

5. The process of claim 1, wherein the molar ratio (meth)acrylic acid anhydride: substrate in step (a) is between 5:1 and 1:5.

6. The process of claim 1, wherein the molar ratio (meth)acrylic acid anhydride: substrate in step (a) is between 3:1 and 1:3.

7. The process of claim 2, wherein the total amount of the first catalyst in step (a) is between 0.001 mol.-% and 10 mol.-% based on the amount of the substrate.

8. The process of claim 7, wherein the total amount of the first catalyst in step (a) is between 0.01 mol.-% and 1.0 mol.-%, based on the amount of the substrate.

9. The process of claim 2, wherein the molar ratio (meth)acrylic acid anhydride: substrate in step (a) is between 5:1 and 1:5.

10. The process of claim 2, wherein the molar ratio (meth)acrylic acid anhydride: substrate in step (a) is between 3:1 and 1:3.

11. A process for the preparation of a (meth)acrylic acid ester, comprising at least step (a) as follows:
(a) reacting a (meth)acrylic acid anhydride of Formula (I):

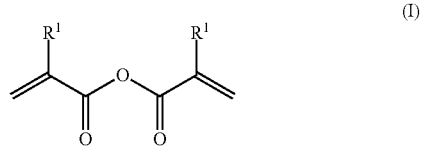

wherein $R^1$ is a hydrogen atom or a methyl group;
with a substrate in the presence of a first catalyst to form a product mixture comprising the (meth)acrylic acid ester; and wherein:
the substrate is a secondary alcohol having one hydroxyl group or a tertiary alcohol having one hydroxyl group; and
the first catalyst comprises a halide of magnesium;
wherein the temperature during step (a) is kept between 60° C. and 90° C.

12. The process of claim 11, wherein the first catalyst is selected from the group consisting of: magnesium bromide; magnesium iodide; and magnesium chloride.

13. The process of claim 12, wherein the reaction shows a conversion of greater than 18%.

14. The process of claim 11, wherein the total amount of the first catalyst in step (a) is between 0.001 mol.-% and 10 mol.-% based on the amount of the substrate.

15. The process of claim 11, wherein the total amount of the first catalyst in step (a) is between 0.01 mol.-% and 1.0 mol.-%, based on the amount of the substrate.

16. The process of claim 11, wherein the molar ratio (meth)acrylic acid anhydride: substrate in step (a) is between 5:1 and 1:5.

17. The process of claim 11, wherein the molar ratio (meth)acrylic acid anhydride: substrate in step (a) is between 3:1 and 1:3.

18. The process of claim 11, wherein the substrate is a secondary alcohol having one hydroxyl group.

19. The process of claim 11, wherein the substrate is a tertiary alcohol having one hydroxyl group.

* * * * *

UNITED STATES PATENT AND TRADEMARK OFFICE
CERTIFICATE OF CORRECTION

PATENT NO. : 11,884,618 B2
APPLICATION NO. : 17/750273
DATED : January 30, 2024
INVENTOR(S) : Treskow et al.

It is certified that error appears in the above-identified patent and that said Letters Patent is hereby corrected as shown below:

In the Specification

In Column 5, Lines 12-13 should read as follows: Preparation of A Stock Solution of Methanol and Methacrylic Anhydride 156 g (1.0 mol) of natural menthol and....

In Column 7, Lines 64-65 "Methacrvlic" should read: "Methacrylic".

In Column 8, Line 1 "teat" should read: "tert".

In Column 11, Lines 33-34 should read as follows: Preparation of A Stock Solution of Hexafluoroisopropanol and Methacrylic Anhydride 50.4 g (0.30 mol) of hexafluoroisopropanol....

In Column 11, Line 34 "Methacrviic" should read: "Methacrylic".

In Column 12, Line 30 "tent" should read: "tert".

In Column 13, Line 29 "Methacrvlic" should read: "Methacrylic".

Signed and Sealed this
Tenth Day of September, 2024

Katherine Kelly Vidal
*Director of the United States Patent and Trademark Office*